(12) United States Patent
Tang et al.

(10) Patent No.: US 11,317,858 B2
(45) Date of Patent: May 3, 2022

(54) MEDICAL MONITORING DEVICE AND METHOD AND SYSTEM FOR DISPLAYING PATIENT MONITORING INFORMATION

(71) Applicant: SHENZHEN MINDRAY BIO-MEDICAL ELECTRONICS CO., LTD., Shenzhen (CN)

(72) Inventors: Xiaocheng Tang, Shenzhen (CN); Ming Yi Tan, Shenzhen (CN); Weijun Wu, Shenzhen (CN); Jianhui Zhang, Shenzhen (CN); Qinglin Tao, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 231 days.

(21) Appl. No.: 16/292,652

(22) Filed: Mar. 5, 2019

(65) Prior Publication Data
US 2019/0216390 A1    Jul. 18, 2019

Related U.S. Application Data

(63) Continuation of application No. PCT/CN2016/098135, filed on Sep. 5, 2016.

(51) Int. Cl.
*A61B 5/00* (2006.01)
*A61B 5/02* (2006.01)
(Continued)

(52) U.S. Cl.
CPC .............. *A61B 5/4821* (2013.01); *A61B 5/00* (2013.01); *A61B 5/02* (2013.01); *A61B 5/02055* (2013.01);
(Continued)

(58) Field of Classification Search
CPC ........... A61B 5/4821; A61B 5/00; A61B 5/02; A61B 5/02055; A61B 5/14551;
(Continued)

(56) References Cited

U.S. PATENT DOCUMENTS

| 5,522,387 A | 6/1996 | Simons |
| 8,512,240 B1 * | 8/2013 | Zuckerman-Stark ....................... G16H 40/63 600/301 |

(Continued)

FOREIGN PATENT DOCUMENTS

| CN | 101138522 A | 3/2008 |
| CN | 202288276 A | 7/2012 |

(Continued)

OTHER PUBLICATIONS

Mary Mark Ockerbloom, Capnography, http://en.wikipedia.org/w/index.php?title=Capnography&oldid=668305992, Jun. 23, 2015, Visited Date: Dec. 3, 2020, 5 pages.

*Primary Examiner* — Gary Jackson
*Assistant Examiner* — Sebastian X Lukjan
(74) *Attorney, Agent, or Firm* — Kory D. Christensen

(57) ABSTRACT

A medical monitoring device includes a signal collection module, a data processing module and a display module. The data processing module processes a vital sign signal collected by the signal collection module, generates physiological parameters, and generates visualization information about parameters of interest corresponding to a designated anesthetic phase based on request information, the designated anesthetic phase is an anesthetic induction phase, an anesthetic maintenance phase or a postoperative recovery phase, and the parameters of interest comprise parameters selected from the physiological parameters and/or anesthetic parameters derived from the physiological parameters. The display module at least displays the visualization informa- (Continued)

tion about the parameters of interest corresponding to the designated anesthetic phase in an anesthetic state display area.

20 Claims, 12 Drawing Sheets

(51) Int. Cl.
 G16H 40/63 (2018.01)
 A61B 5/0205 (2006.01)
 A61B 5/1455 (2006.01)
 A61B 5/021 (2006.01)
 A61B 5/024 (2006.01)

(52) U.S. Cl.
 CPC .......... *A61B 5/14551* (2013.01); *A61B 5/743* (2013.01); *A61B 5/7435* (2013.01); *G16H 40/63* (2018.01); *A61B 5/021* (2013.01); *A61B 5/024* (2013.01); *A61B 5/02405* (2013.01); *A61B 5/4824* (2013.01)

(58) Field of Classification Search
 CPC ... A61B 5/7435; A61B 5/021; A61B 5/02405; A61B 5/4824; A61B 5/024; G16H 40/63
 See application file for complete search history.

(56) References Cited

U.S. PATENT DOCUMENTS

| | | | |
|---|---|---|---|
| 2006/0217628 A1* | 9/2006 | Huiku | A61B 5/4839 600/544 |
| 2007/0276609 A1* | 11/2007 | Greenwald | A61B 5/048 702/19 |
| 2009/0177108 A1* | 7/2009 | Shieh | A61B 5/4821 600/544 |
| 2010/0022849 A1* | 1/2010 | Franz | A61B 5/0205 600/300 |
| 2010/0169063 A1* | 7/2010 | Yudkovitch | A61M 16/085 703/11 |
| 2010/0201524 A1* | 8/2010 | Gallagher | A61B 5/113 340/573.1 |
| 2014/0012096 A1* | 1/2014 | Nomura | A61B 5/742 600/301 |
| 2016/0012189 A1* | 1/2016 | Farha | G16H 70/20 705/2 |
| 2016/0174856 A1* | 6/2016 | Huang | A61B 5/7257 600/479 |

FOREIGN PATENT DOCUMENTS

| | | |
|---|---|---|
| CN | 103040460 A | 4/2013 |
| CN | 103893873 A | 7/2014 |
| CN | 104116502 A | 10/2014 |
| CN | 103040460 A | 6/2015 |
| CN | 204654929 U | 9/2015 |
| CN | 105413030 A | 3/2016 |
| EP | 0633540 A2 | 1/1995 |
| WO | WO 2013/119978 A1 | 8/2013 |
| WO | WO-2015087206 A1 * | 6/2015 ............... A61B 6/12 |
| WO | WO 2016000185 A1 | 1/2016 |
| WO | WO-2016109177 A2 * | 7/2016 ............ A61M 16/22 |

* cited by examiner

MEDICAL MONITORING DEVICE AND METHOD AND SYSTEM FOR DISPLAYING PATIENT MONITORING INFORMATION

CROSS-REFERENCE TO RELATED APPLICATIONS

This application is a continuation of Patent Cooperation Treaty (PCT) App. No. PCT/CN2016/098135, filed Sep. 5, 2016, for "MEDICAL MONITORING DEVICE, AND METHOD AND SYSTEM FOR DISPLAYING PATIENT MONITORING INFORMATION," which is incorporated herein by reference.

TECHNICAL FIELD

The present disclosure relates to medical monitoring, and in particular to a medical monitoring device, a method, and a system for displaying patient monitoring information.

BACKGROUND

In order to control and reduce the risk of clinical anesthesia, individual anesthesia monitoring standards or monitoring guidelines have been developed both internationally and domestically, requiring strict monitoring of vital sign indexes of a patient. Studies have shown that failure to timely and comprehensively monitor the patient during anesthesia is one of the primary causes of perioperative anesthesia complications. By strengthening the monitoring, measures can be timely taken in accordance with the monitoring results to reduce the incidence of adverse reactions or anesthesia accidents in order to reduce the mortality of anesthesia and ensure the safety of the patient.

Depending on the situation, the current monitoring parameters for the patient undergoing general anesthesia in surgery may include non-invasive blood pressure, respiratory rate, heart rate, blood oxygen saturation, urine volume, central venous pressure, invasive arterial pressure, partial pressure of end-tidal carbon dioxide, body temperature, brain function, respiratory mechanics parameters, muscle relaxation parameters, blood biochemical parameters, cardiac output, and anesthetic gas concentration.

The patient's conventional physiological parameters, such as blood pressure, heart rate, and blood oxygen saturation, are typically monitored in real time using a multi-parameter monitor. Waveforms, values, trends and other information associated with the monitored physiological parameters are displayed on a display screen of the multi-parameter monitor.

In some cases, there is a need for a BIS (bispectral index) single-parameter monitor and an NMT (neuromuscular transmission) single-parameter monitor to monitor and display states of the consciousness and muscle relaxation of the patient. Whether in a pre-operative induction phase, in an intraoperative anesthesia maintenance phase, or in a post-operative recovery phase, a physician needs to view these parameters and make judgments about the patient's condition based on the monitored parameters.

In the process of continuous development and improvement of monitoring devices, the inventors found that since the parameters monitored for anesthetized patients are numerous and may be allocated to different monitors, the physician often views these numerous parameters one by one, selects and combines required parameter information from the numerous parameters according to experience, and then makes a comprehensive judgment on the patient's anesthesia state, which makes the physician have to take a long time to judge the patient's anesthesia state, thereby affecting the physician's rapid reaction and response to the patient's abnormal condition.

BRIEF SUMMARY

The technical problem to be solved by the present disclosure is to provide a medical monitoring device and a method and a system for displaying patient monitoring information for assisting a physician in accelerating the judgment of an anesthesia state of a patient.

According to one aspect, a medical monitoring device may include a signal collection module configured to collect patient's vital sign signals from the body of a patient. The medical monitoring device may further include a data processing module connected to the signal collection module and configured to receive the vital sign signals and process the vital sign signals to generate physiological parameters for reflecting the condition of the patient, the data processing module being further configured to receive request information for requesting display of a designated anesthetic phase and generate, based on the request information, visualized information about parameters of interest corresponding to the designated anesthetic phase, the designated anesthetic phase being an anesthetic induction phase before surgery, an anesthetic maintenance phase during surgery, or a postoperative recovery after surgery, and the parameters of interest including parameters selected from the physiological parameters and/or anesthetic parameters derived from the physiological parameters.

The medical monitoring device may also include a display module including a display interface. The display module may be connected to the data processing module and may be configured to receive the visualized information outputted by the data processing module and display in an anesthetic state display area at least the visualized information about the parameters of interest corresponding to the designated anesthetic phase. In one embodiment, the anesthetic state display area is at least a partial area of the display interface of the monitoring device.

According to another aspect, a method for displaying patient monitoring information may include acquiring vital sign signals collected from the body of a patient and processing the vital sign signals to generate physiological parameters for reflecting condition of the patient. In one embodiment, the method may also include receiving request information for requesting display of a designated anesthetic phase, the designated anesthetic phase being an anesthetic induction phase before surgery, an anesthetic maintenance phase during surgery, or a postoperative recovery phase after surgery.

In one embodiment, the method includes generating, based on the request information, visualized information about parameters of interest corresponding to the designated anesthetic phase. The parameters of interest may include parameters selected from the physiological parameters and/or anesthetic parameters derived from the physiological parameters.

The method may further include displaying in an anesthetic state display area the visualized information about the parameters of interest corresponding to the designated anesthetic phase, the anesthetic state display area being at least a partial area of a display interface of a monitoring device.

According to yet another aspect, a system for displaying patient monitoring information may include an information acquisition unit configured to acquire vital sign signals collected from the body of a patient; a first information processing unit configured to process the vital sign signals to generate physiological parameters for reflecting the condition of the patient; a request unit configured to receive request information for requesting display of a designated anesthetic phase, the designated anesthetic phase being an anesthetic induction phase before surgery, an anesthetic maintenance phase during surgery, or a postoperative recovery phase after surgery.

In one embodiment, the system may further include a second information processing unit configured to generate, based on the request information, visualized information about parameters of interest corresponding to the designated anesthetic phase, the parameters of interest including parameters selected from the physiological parameters and/or anesthetic parameters derived from the physiological parameters.

The system may further include a display unit, configured to display in an anesthetic state display area the visualized information about the parameters of interest corresponding to the designated anesthetic phase, the anesthetic state display area being at least a partial area of a display interface of a monitoring device.

In the embodiments of the present disclosure, since the respective parameters of interest are set for each anesthetic phase, and the current anesthesia state of the patient can be reflected by these parameters of interest, when a certain anesthetic phase needs to be displayed, the parameters of interest related to this anesthetic phase can be displayed on the same screen and intuitively presented to the physician, so that the physician can determine at a glance whether the patient is acting abnormally during the anesthetic phase, whether the anesthesia is appropriate, or the like.

DETAILED DESCRIPTION

Figure 1:
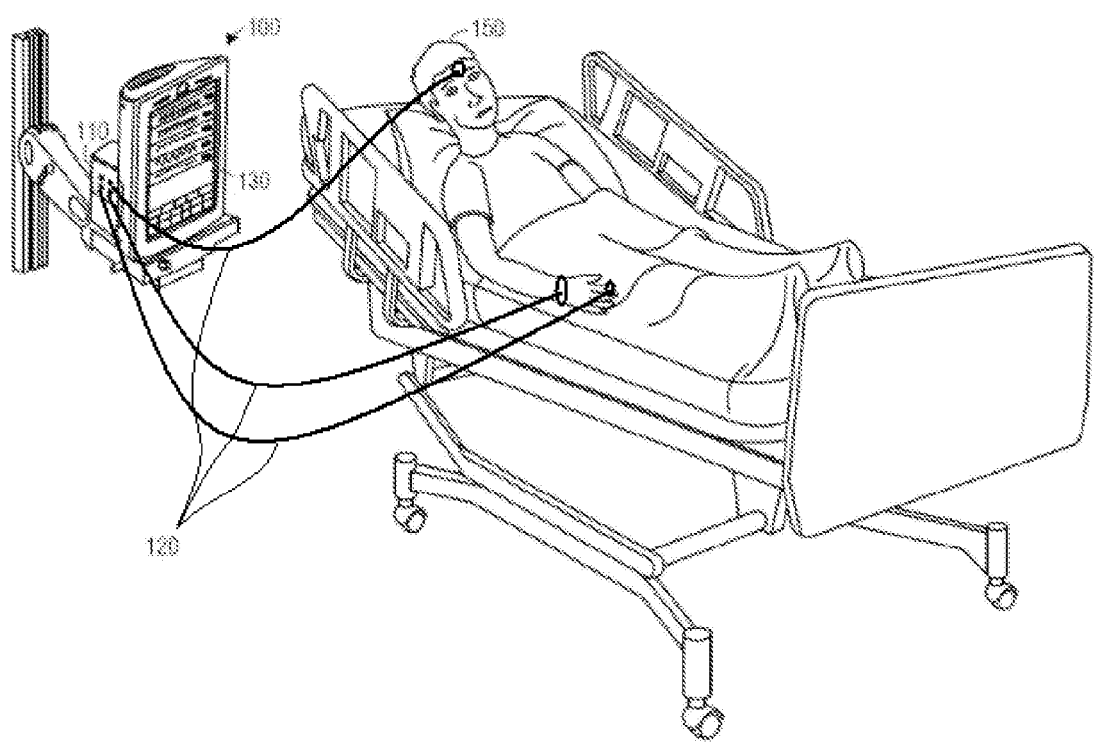
FIG. 1 is a schematic structural diagram of a medical monitoring device in one embodiment.

Embodiments of the disclosure are described in detail below with specific embodiments and in conjunction with the accompanying drawings. Similar elements in various embodiments use associated similar component element reference signs. In the following embodiments, many details are described so that the present application can be better understood. However, it will be understood by those skilled in the art that some features may be omitted in different cases, or may be substituted by other elements, materials, and methods. In certain cases, some operations relevant to the present application are not shown or described in the description, and this is to prevent the core part of the application from being obscured by too much description. However, for those skilled in the art, the detailed description of these relevant operations is not necessary, and they may completely understand relevant operations according to the description and general technical knowledge in the art.

In addition, certain characteristics, operations, or features described in the description may be combined in any appropriate manner to form various embodiments. Moreover, the steps or actions in the method description may also be exchanged or adjusted in order in a way that would be understood to those skilled in the art. Therefore, various orders in the description and accompanying drawings are merely exemplary and not necessary unless specified otherwise that a certain order must be followed.

For a patient undergoing general anesthesia, there are usually three phases, namely, an anesthetic induction phase before surgery, an anesthetic maintenance phase during surgery, and a postoperative recovery phase after surgery.

In the anesthetic induction phase, a physician will do the following operations:

1. Preoxygenation and denitrogenation: breathing oxygen is supplied via a mask to ensure oxygen supply throughout the induction process.

2. Anesthetic administration: an anesthetist administrates an intravenous anesthetic or inhalational anesthetic, an analgesic, and a muscle relaxant to the patient, such that the patient's consciousness gradually disappears, the sense of pain is passivated until it disappears, and the muscle tension is gradually weakened.

3. Endotracheal intubation: upon the patient's consciousness reaches the appropriate depth, and analgesia and muscle relaxation are both completed, the anesthetist administrates an endotracheal intubation to the patient to complete the induction process.

The requirements for the anesthetic induction phase are that the entire induction process is coherent and the patient's vital signs are stable.

The requirements for the anesthetic maintenance phase include maintaining the appropriate depth of consciousness, and the complete analgesia and muscle relaxation of the patient during surgery to meet the surgical requirements; and maintaining the stability of the vital signs of the patient during surgery to ensure the life safety of the patient.

The requirements for the postoperative recovery phase are that after the surgery is completed, the anesthetist gradually reduces the anesthetic to the patient until the administration of the anesthetic is stopped. By monitoring the patient's vital signs, BIS, NNT, respiratory parameters, etc., when it is determined that the patient's vital signs are stable, the consciousness is restored, spontaneous breathing is established, and the muscle tension is restored, an extubation is performed; and after the extubation, the monitoring of the important vital signs is continued.

During the development of the present disclosure, the inventors have, based on clinical experience, realized that due to the different requirements and operations performed at each phase, the physician is concerned with different information when evaluating the condition of the patient at each phase. Therefore, on aspect of the present disclosure is to exhibit information about the parameters of interest related to the anesthetic phase on the display interface when there is a need to evaluate the condition of the patient in a certain anesthetic phase or when there is a need to perform the anesthesia monitoring for a certain phase.

In other words, each anesthetic phase has its own corresponding parameters of interest. When the physician needs to understand the anesthesia state of the patient, he/she no longer has to view the numerous parameters one by one. Instead, the parameters of interest corresponding to each anesthetic phase are processed to generate visualized information, displayed in the anesthetic state display area on the same screen and intuitively presented to the physician, so that the physician can quickly determine at a glance whether the patient is acting abnormally during the anesthetic phase, whether the anesthesia is appropriate, etc.

These parameters of interest may include existing physiological parameters monitored by the monitoring device in real time, or parameters obtained by integrating parameters monitored by an external device into this monitoring device. The parameters of interest may also be parameters calculated or statistically derived according to the existing physiological parameters, or may be parameters obtained by integrating the parameters monitored by the external device into the monitoring device.

The parameters calculated or statistically derived according to the existing physiological parameters will be collectively referred to as anesthetic parameters herein. The parameters of interest for each phase are set up in advance in the system based on clinical experience, and in some embodiments, the physician may also be allowed to modify the parameters of interest. In other words, when in use, the physician can use the default parameters of interest corresponding to each anesthetic phase, or alter the parameters of interest corresponding to a certain phase according to his/her own needs.

For a patient undergoing general anesthesia, the monitoring of the anesthetic state may be performed for all the three phases using the principles disclosed herein, or the monitoring of the anesthetic state may be performed only for any two of the phases by implementing principles of the present disclosure. For example, the monitoring of the anesthetic state may be performed for the anesthetic induction phase and the anesthetic maintenance phase, or the monitoring of the anesthetic state may performed for the anesthetic maintenance phase and the postoperative recovery phase. As an example, the monitoring of the anesthetic state being performed for all the three phases will be described below.

First Embodiment

Referring to FIG. 1, there is shown a medical monitoring device 100 for monitoring a patient 150. The medical monitoring device 100 may include a data processing module 110, a signal collection module 120 and a display module 130.

One end of the signal collection module 120 is used to make contact with the body of the patient to collect, from the body of the patient, patient's vital sign signals such as a pulse signal caused by the heartbeat, a body temperature signal, a blood absorption signal for a specific band of light, an electrocardiogram signal, and an electroencephalogram signal. The other end of the signal collection module 120 is connected to the data processing module 110, for example, to the data processing module 110 via an interface, and the vital sign signals are input to the data processing module 110.

The data processing module 110 is connected to the signal collection module 120 and the display module 130, respectively, receives the vital sign signals, processes the vital sign signals, generates physiological parameters for reflecting the condition of the patient, and processes the physiological parameters into visualized data. The visualized data is then sent to the display module 130, such that the display module 130 displays the visualized data on a display interface. The conventional physiological parameters include, for example, blood pressure, blood oxygen saturation, heart rate, body temperature, electrocardiogram, etc.

The display module 130 includes a display screen that provides the display interface. The display screen may be of a touch or non-touch type.

In this embodiment, the data processing module 110 further receives request information for requesting display of a designated anesthetic phase and generates, based on the request information, visualized information about parameters of interest corresponding to the designated anesthetic phase, the designated anesthetic phase being an anesthetic induction phase before surgery, an anesthetic maintenance phase during surgery, or a postoperative recovery after surgery, and the parameters of interest including parameters selected from the physiological parameters and/or anesthetic parameters derived from the physiological parameters.

The physiological parameters may be the existing physiological parameters monitored by the monitoring device in real time, or may be physiological parameters obtained by integrating parameters monitored by an external device into the monitoring device. The data processing module 110 sends the visualized information about the parameters of interest to the display module 130. The display module 130 allocates at least a partial area as an anesthetic state display area on the display interface thereof, and displays the visualized information about the parameters of interest in the anesthetic state display area.

Figure 2:
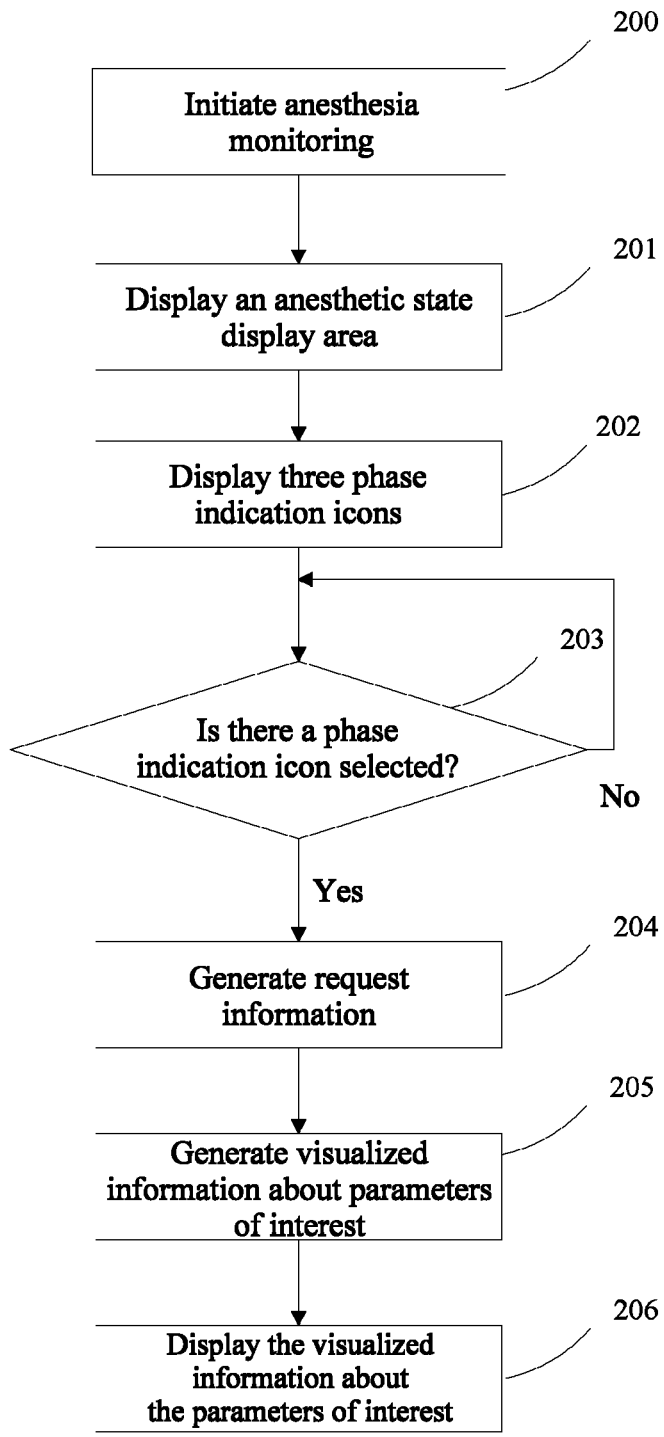
FIG. 2 is a flow chart showing the display of patient anesthesia monitoring information in one embodiment.

In one embodiment, the display of the patient anesthesia monitoring information is implemented by computer software. A method for displaying the monitoring information is shown in FIG. 2 and includes the following steps:

Step 200, in which anesthesia monitoring is initiated. A start icon 137 for initiating the anesthesia monitoring is provided in the display interface, as shown in FIG. 3, and a request for initiating the anesthesia monitoring is triggered by the operator selecting the start icon. The display module 130 detects that the start icon is triggered by the operator, generates the request for initiating the anesthesia monitoring, and sends the request to the data processing module 110.

Step 201, in which at least one anesthetic state display area 132 is allocated on the display interface 131 of the monitoring device when it is detected that the start icon is selected. After receiving the request, the data processing module 110 outputs display data to the display module, such that the display module divides the display interface into the at least one anesthetic state display area 132.

Figure 3A:
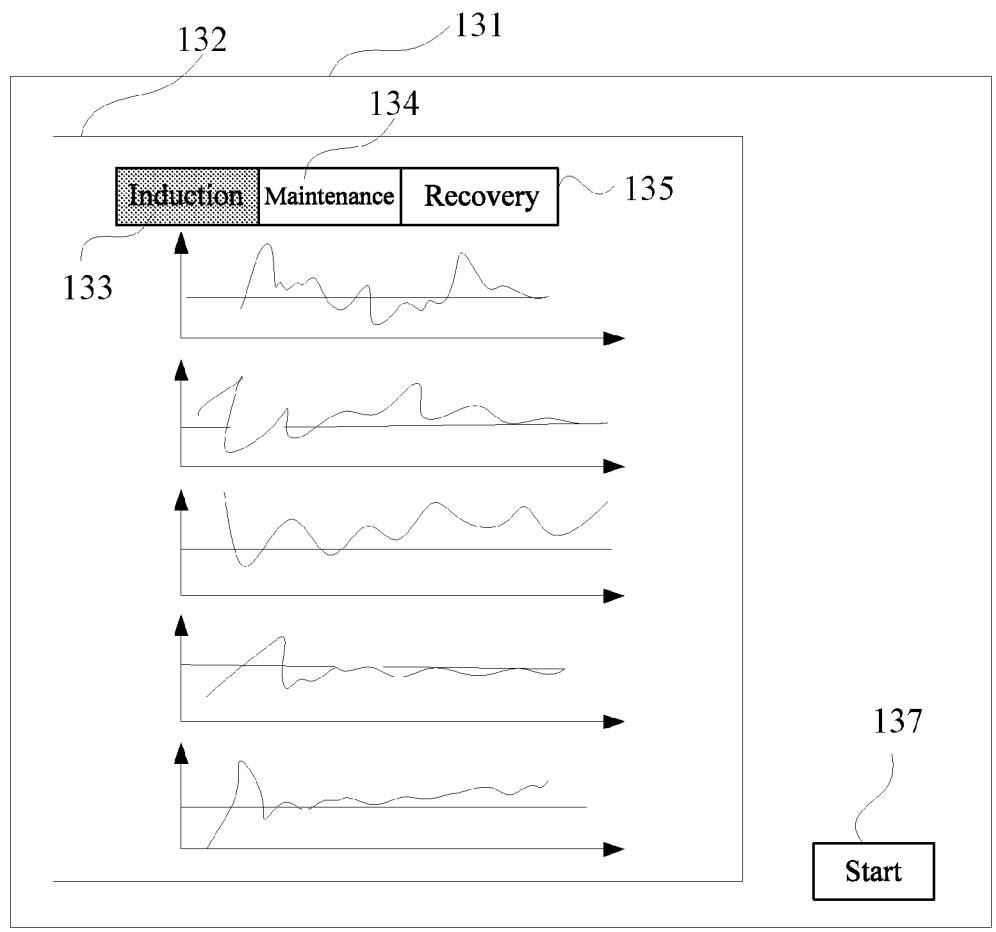
FIG. 3A is a schematic diagram of an anesthetic state display area in one embodiment.
Figure 3B:
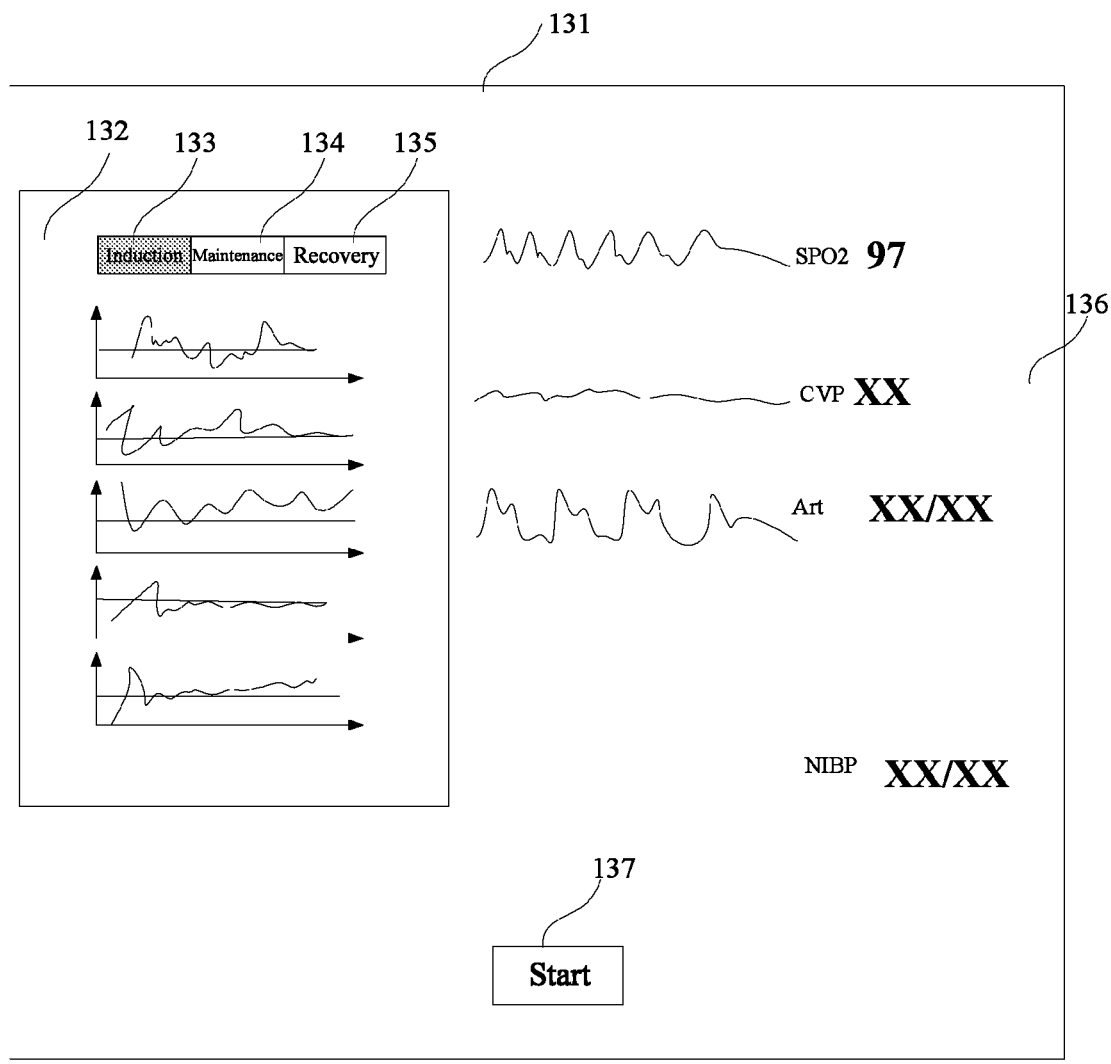
FIG. 3B is a schematic diagram of an anesthetic state display area in another embodiment.

The anesthetic state display area may be the entire area of the display interface, as shown in FIG. 3A. The anesthetic state display area may also be only a partial area of the display interface. For example, the display interface 131 may include at least one anesthetic state display area 132 and a conventional display area 136. As shown in FIG. 3B, parameters of interest for a selection phase are displayed in the anesthetic state display area 132. The conventional display area 136 may be used to display the physiological parameters monitored by the monitoring device in real time, such as a beat of each heartbeat, a waveform or a real-time value of a blood pressure, a blood oxygen saturation, a heart rate, a body temperature, etc.

Step 202, in which three phase indication icons are displayed in the anesthetic state display area 132. As shown in FIG. 3, an "induction" icon 133 represents the anesthetic induction phase, a "maintenance" icon 134 represents the anesthetic maintenance phase, and a "recovery" icon 135 represents the postoperative recovery phase. Those skilled in the art should understand that in other embodiments, when the anesthesia monitoring is performed only in two phases, only two phase indication icons may be displayed in the anesthetic state display area 132. For example, only the "induction" icon 133 and the "maintenance" icon 134 may be displayed, or only the "maintenance" icon 134 and the "recovery" icon 135 may be displayed.

Step 203, in which it is detected whether a phase indication icon is selected. The operator can select the phase indication icon by manipulating a cursor. When the display module includes a touch screen, the operator can also select the phase indication icon by touching the screen. When a phase indication icon is selected, the selected phase indication icon is highlighted using an interface element different from the other phase indication icons. For example, it is highlighted using a different color, or a different fill pattern, a different gray level, or the like.

Step 204, in which when a phase indication icon is selected, request information for requesting display of the designated anesthetic phase is generated. The display module 130 detects an operator's trigger on the phase indication icon. When a phase indication icon is selected, the display module generates corresponding request information and sends the request information to the data processing module 110. When the "induction" icon 133 is selected, request information for requesting display of the anesthetic induction phase is generated. When the "maintenance" icon 134 is selected, request information for requesting display of the anesthetic maintenance phase is generated. When the "recovery" icon 135 is selected, request information for requesting display of the postoperative recovery phase is generated.

Step 205, in which visualized information about the parameters of interest corresponding to the designated anesthetic phase is generated based on the request information. After receiving the request information, the data processing module 110 parses the request information, determines the anesthetic phase needing to be displayed, and then determines the parameters of interest corresponding to the anesthetic phase in accordance with a pre-set correspondence table. The parameters of interest can be directly acquired from the conventional physiological parameters if they already exist in the conventional physiological parameters, or obtained by mathematical means such as calculation or statistics according to the conventional physiological parameters if they are yet not in the conventional physiological parameters.

Each parameter of interest includes a parameter name, a detection time point, and a parameter value corresponding to the time point. After obtaining the parameters of interest, the data processing module 110 processes the parameters of interest into corresponding visualized information according to the manner required to be presented, and outputs the visualized information to the display module.

Step 206, in which the visualized information about the parameters of interest corresponding to the designated anesthetic phase is displayed in the anesthetic state display area.

After receiving the visualized information, the display module 130 processes the visualized information into frame data and displays same on the display interface.

When the "induction" icon 133 is selected, the visualized information about the parameters of interest for the anesthetic induction phase is displayed in the anesthetic state display area. In this embodiment, the parameters of interest for the anesthetic induction phase include heart rate (HR), blood oxygen saturation ($SPO_2$), blood pressure (NIBP), body temperature (TEMP), bispectral index (BIS), and patient suffocation time. Heart rate, blood oxygen saturation, blood pressure, body temperature and bispectral index are parameters selected from the conventional physiological parameters, which can be directly obtained from the detected conventional physiological parameters.

The patient suffocation time is an anesthetic parameter obtained according to the detected respiratory signal. Heart rate, blood oxygen saturation, blood pressure, body temperature and bispectral index are used to assess whether the patient's vital signs are stable. Patient suffocation time is used to evaluate whether the patient has suffocated.

In the anesthetic induction phase, one of the operations that the physician needs to do is endotracheal intubation. In other words, upon the patient's consciousness reaches the appropriate depth, and analgesia and muscle relaxation are both completed, the anesthetist performs an endotracheal intubation of the patient. During endotracheal intubation, the patient stops breathing, but the patient does not stop breathing for too long, otherwise the patient is at risk of life, so the patient suffocation time needs to be monitored. Once the suffocation time exceeds a certain length of time, the intubation is stopped immediately, and oxygen is supplied to the patient via a mask.

Figure 4:
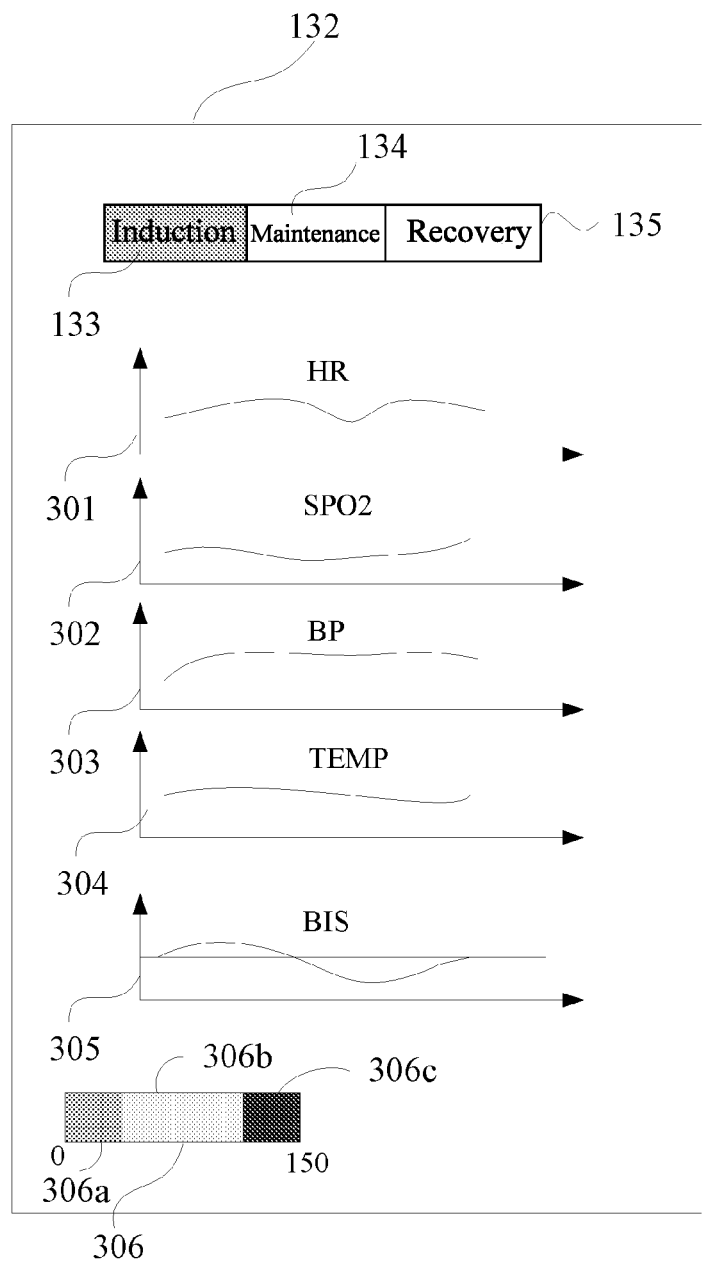
FIG. 4 is a schematic diagram showing the display of parameters of interest for an anesthetic induction phase in one embodiment.

In this embodiment, as shown in FIG. 4, heart rate 301, blood oxygen saturation 302, blood pressure 303, body temperature 304 and bispectral index 305 are respectively displayed in the form of trend graphs in the anesthetic state display area 132. For example, the horizontal axis represents time and the vertical axis represents the value of the parameter of interest, and the point on the curve represents the parameter value of the parameter of interest at that time.

The display time of the trend graph may be the time of the entire anesthetic induction phase, or may be a determined period of time before or after the current time. The patient suffocation time 306 is displayed in the form of a time progress bar in the anesthetic state display area, and a normal zone 306a, a warning zone 306b and a danger zone 306c are marked on the time bar in the time progress direction.

The warning zone represents a period of time for which the patient is allowed to suffocate, and the length of time of the warning zone is set according to the type of the patient, for example, 120 seconds for adults, 30 seconds for children, and 20 seconds for newborns. The danger zone represents a period of suffocation time for which the patient may be in danger. When the progress pointer enters the danger zone, it indicates that the patient has a long suffocation time and is in danger.

The normal zone 306a, the warning zone 306b and the danger zone 306c may be clearly distinguished by different colors or patterns. For example, the normal zone 306a is represented by green, the warning zone 306b is represented by yellow, and the danger zone 306c is represented by red. In various applications, when the signal collection module 120 detects a respiratory signal, the data processing module 110 starts timing, and outputs a display signal such that the display module 130 moves the progress pointer along the time bar according to the timing time from the 0 coordinate of the time bar. When the signal collection module 120 detects a next respiratory signal, the data processing module 110 outputs a display signal such that the display module 130 resets the progress pointer to the 0 coordinate. In an alternative embodiment, when the progress pointer enters the danger zone, the monitoring device may issue an alarm alerting the on-site physician.

In this embodiment, the patient suffocation time is displayed in the form of a time progress bar, which enables the physician to intuitively observe the current suffocation time of the patient, so as to quickly determine whether the operation of the endotracheal intubation needs to be stopped. Therefore, the time progress bar of the suffocation time is also called a suffocation indicator.

In other embodiments, the patient suffocation time may also be displayed in the form of values in the anesthetic state display area.

In some embodiments, if there is a calculated breathing time in the conventionally detected physiological parameters, it is generally provided with a breathing alarm. In other words, a threshold is set in advance, and an alarm is issued when the breathing time exceeds the threshold. Since this threshold is set for normal breathing, it is not generally suitable for respiratory monitoring in the endotracheal intubation. Since the physician usually provides a large amount of oxygen to the patient by artificially assisted breathing before the endotracheal intubation, the patient can extend the suffocation time with the support of this large amount of oxygen to provide a longer intubation time for the physician.

Accordingly, in an alternative embodiment, when the monitoring of the anesthetic induction phase is performed, the patient suffocation time is detected, and the breathing alarm is also masked, or the breathing alarm threshold is altered such that the breathing alarm threshold is greater than or equal to the maximum time value of the warning zone, thereby allowing the suffocation-related physiological alarm to be masked within a rational time range to avoid alarm interference caused by suffocation during intubation.

Certainly, in some embodiments, the parameters of interest for the anesthetic induction phase may also not include the patient suffocation time, i.e., the patient suffocation time is not displayed in the anesthetic state display area, and whether the patient suffocation time is too long determined only based on a monitoring alarm for the breathing. In this case, however, the physician can't intuitively see how much the patient suffocation time is.

In some embodiments, the parameters of interest for the anesthetic induction phase may also include a timer that supports the timing of a user to start, pause and stop, and assists the physician to determine the drug onset time, intubation time, etc.

In some embodiments, the parameters of interest for the anesthetic induction phase may also not include the body temperature (TEMP) and the bispectral index (BIS), that is, the trend graphs of the body temperature (TEMP) and the bispectral index (BIS) are not displayed in the anesthetic state display area.

When the "maintenance" icon 134 is selected, the visualized information about the parameters of interest for the anesthetic maintenance phase is displayed in the anesthetic state display area. In this embodiment, three dimensions of information are used to evaluate the condition of the patient in the anesthetic maintenance phase. The three dimensions are a consciousness dimension, a pain dimension and a muscle relaxation dimension, respectively.

The parameters of interest for the anesthetic maintenance phase also correspondingly include a consciousness parameter characterizing the consciousness condition of the patient under anesthesia, a pain parameter characterizing the pain condition of the patient under anesthesia, and a muscle relaxation parameter characterizing the neuromuscular transmission condition of the patient under anesthesia, the consciousness parameter includes the bispectral index (BIS) and/or a minimum alveolar concentration (MAC), the pain parameter includes at least one of a blood pressure change ($\Delta$NIBP) and a heart rate change ($\Delta$HR), the pain parameter may also be obtained by a dedicated pain monitoring module, and the muscle relaxation parameter includes neuromuscular transmission (NMT), the biospectral index and the neuromuscular transmission may be obtained directly from the conventional physiological parameters, and the blood pressure change and the heart rate change are anesthetic parameters calculated from the blood pressure and the heart rate in the conventional physiological parameters. The blood pressure change refers to the change in blood pressure relative to a blood pressure reference value, the heart rate change is the change in heart rate relative to a heart rate reference value, and the reference values may be parameter values of the patient measured before anesthesia, or may be values set according to clinical experience.

Figure 5:
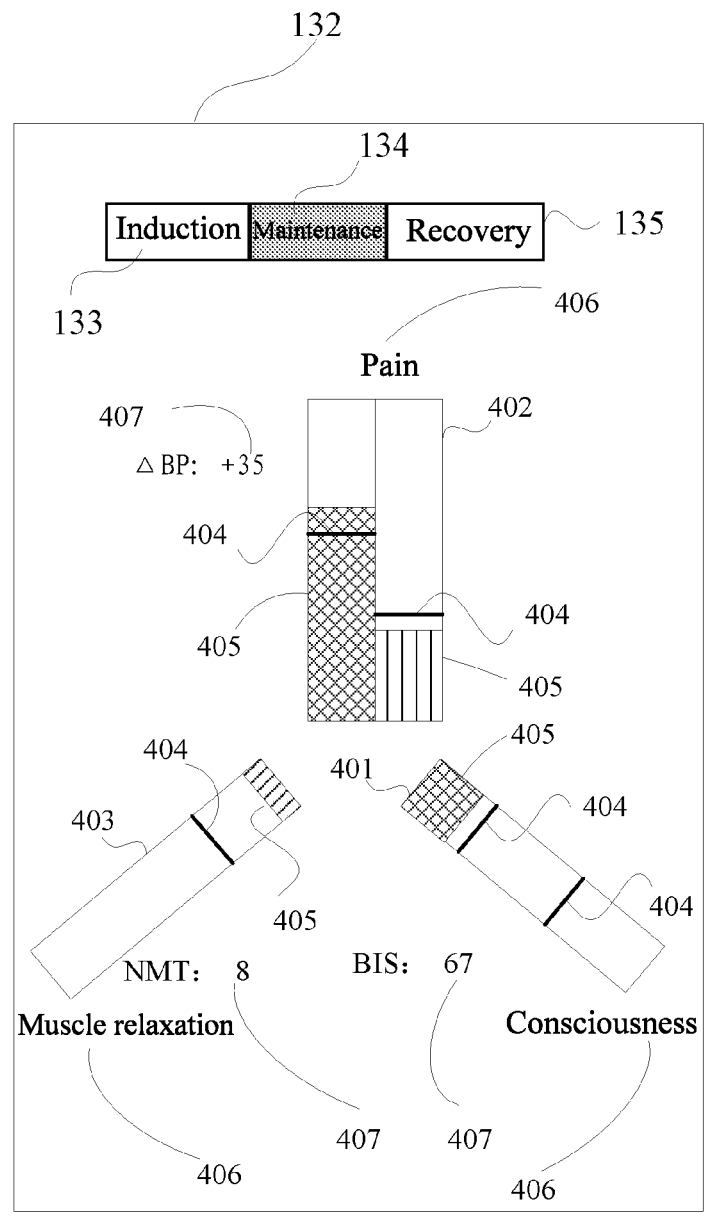
FIG. 5 is a schematic diagram showing the display of parameters of interest for an anesthetic maintenance phase in one embodiment.

As shown in FIG. 5, the anesthetic state display area 132 is divided into three areas for respectively displaying the information about the three dimensions. In this embodiment, current parameter values of the consciousness parameter, the pain parameter and the muscle relaxation parameter are respectively displayed in the form of a graph in the respective area, the bispectral index (BIS) and/or the minimum alveolar concentration (MAC) are/is shown in the area 401, the blood pressure change ($\Delta$NIBP) and the heart rate change ($\Delta$HR) are shown in the area 402, and the neuromuscular transmission (NMT) is shown in the area 403. The graph form uses a histogram, and parameters of the three dimensions form three sets of histograms.

In FIG. 5, the three sets of histograms are arranged in a star shape. In other embodiments, the three sets of histograms may also be arranged in parallel or may be enclosed in a triangle. In the histogram, the histogram and its varying height or length or width is used to reflect the changes of the corresponding parameter, or the histogram is combined with different colors to reflect whether the corresponding parameter is normal, etc.

In the histogram, various markers can also be used to represent the thresholds of the corresponding parameters, such as a horizontal cut line in the histogram is used as the threshold 404 of the parameter, and the parameter value 405 of the corresponding parameter is represented by a color, a pattern or a graphic mark, and whether the corresponding parameter exceeds the threshold and how much is exceeded are represented by the spacing between the color, the pattern or the graphic marker and the horizontal cut line. To clearly display the parameters represented by each histogram, the parameter name 406 is indicated by a text or abbreviated abbreviation next to each histogram. To enable the physician to quickly know the value of each parameter, the parameter value 407 of each parameter may also be indicated next to each histogram.

In a further embodiment, the current parameter values of the consciousness parameter, the pain parameter and the muscle relaxation parameter may also be displayed in their respective regions using other graphical means such as a gage or a sector, and the current parameter values of the consciousness parameter, the pain parameter and the muscle relaxation parameter may also be displayed in the respective areas directly using a text plus a value.

Figure 6:
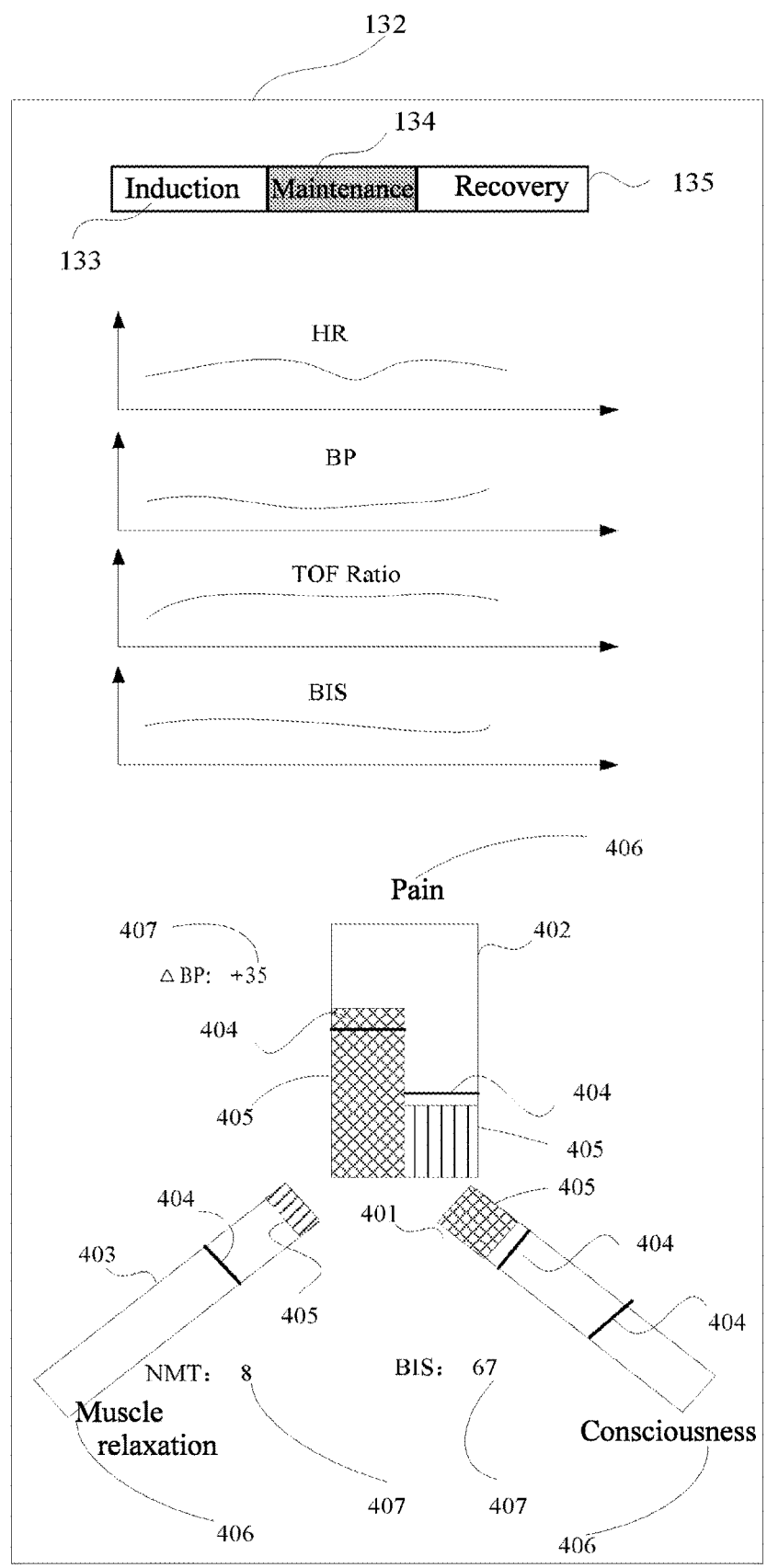
FIG. 6 is a schematic diagram showing the display of parameters of interest for an anesthetic maintenance phase in another embodiment.

In a further embodiment, the parameters of interest for the anesthetic maintenance phase may also include the blood pressure and the heart rate. As shown in FIG. 6, in the anesthetic state display area 132, in addition to displaying the information about the three dimensions, the trend graphs of the bispectral index, the neuromuscular transmission, the blood pressure and the heart rate are also displayed. The display time of the trend graph may be the time of the entire anesthetic maintenance phase, or may be a determined period of time before or after the current time.

When the "recovery" icon 135 is selected, the visualized information about the parameters of interest for the postoperative recovery phase is displayed in the anesthetic state display area. In this embodiment, the parameters of interest for the postoperative recovery phase include heart rate (HR), blood oxygen saturation ($SPO_2$), blood pressure (BP), respiratory rate (RR), bispectral index (BIS), body temperature (TEMP) and a postoperative score result. The heart rate (HR), the blood oxygen saturation ($SPO_2$), the blood pressure (BP), the RR, the bispectral index (BIS), and the body temperature (TEMP) can be obtained directly from the conventional physiological parameters, and the postoperative score result is an anesthetic parameter obtained from the statistics and comparison of the conventional physiological parameters.

Figure 7:
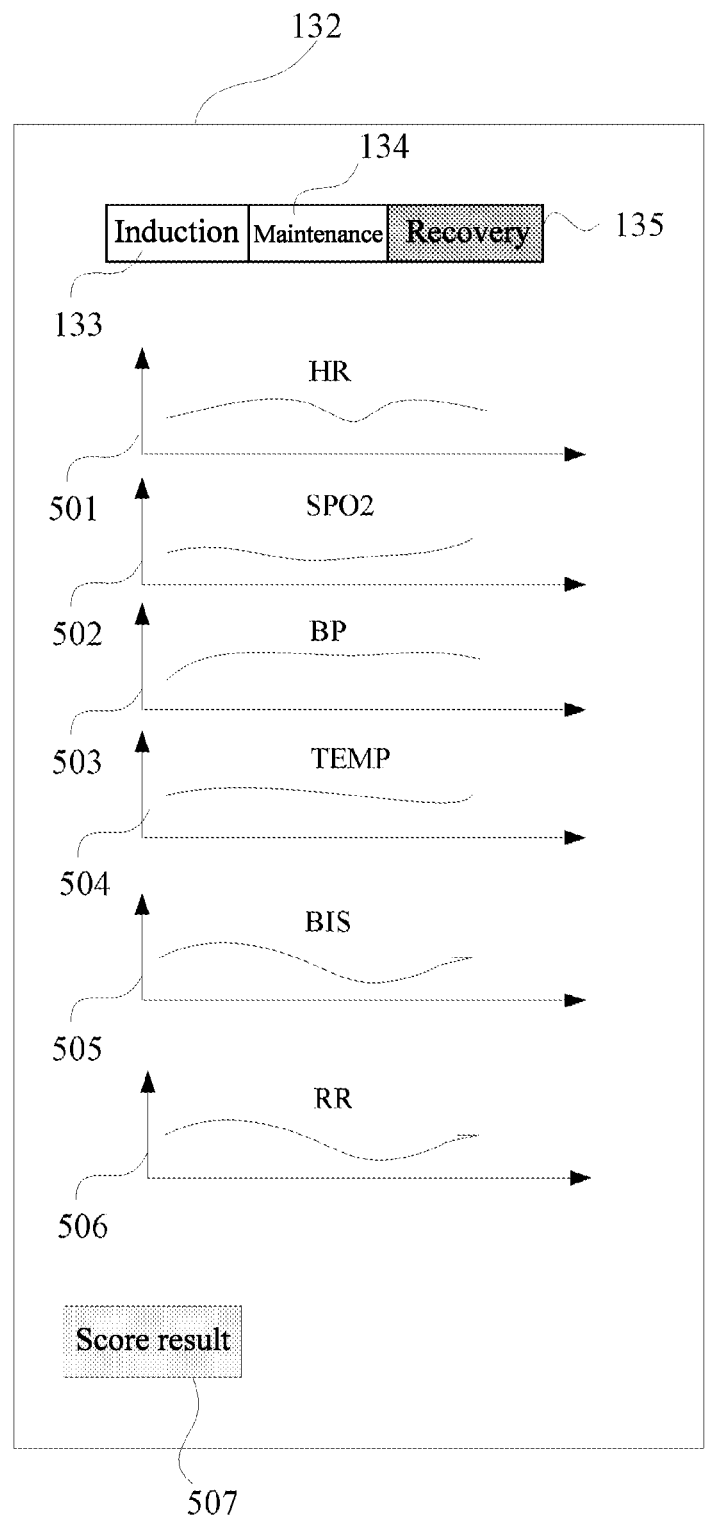
FIG. 7 is a schematic diagram showing the display of parameters of interest for a postoperative recovery phase in one embodiment.

As shown in FIG. 7, the heart rate 501, the blood oxygen saturation 502, the blood pressure 503, the body temperature 504, the bispectral index 505 and the RR 506 are respectively displayed in the form of trend graphs in the anesthetic state display area 132, and the display time of the trend graph may be the time of the entire anesthetic induction phase, or may also be a determined period of time before or after the current time.

The postoperative score result 507 is displayed in the form of an icon in the anesthetic state display area, and a pop-up score sheet is displayed when it is detected that the icon is selected. The score sheet may include a score for each item and a total score. When some sub-items are being scored, automatic scoring can be used. For example, when the blood oxygen saturation is being scored, the data processing module acquires the current parameter value of the blood oxygen saturation of the patient, and compares the current parameter value of the blood oxygen saturation with predetermined scoring criteria. The scoring criteria specifies the scores of various intervals of the parameter value of the blood oxygen saturation, and the data processing module can obtain the score of the current blood oxygen saturation item of the patient according to the scoring criteria. When scores of items are obtained, the data processing module accumulates the scores of the items to obtain the total score of the patient in the current condition.

In a further embodiment, the parameters of interest for the postoperative recovery phase may not include at least one of the respiratory rate (RR), the bispectral index (BIS), the body temperature (TEMP), and the postoperative score result.

In this embodiment, the corresponding parameters of interest are set for each anesthetic phase, and the parameters of interest are displayed in a graphical manner on the same screen to indicate the current anesthetic state of the patient, and provide intuitive and comprehensive information for the physician, so that the physician can see the required information at a glance, without having to look through the screen to find out relevant information to understand the current anesthetic state of the patient. Consequently, the physician can quickly understand the current anesthetic state of the patient while the ease of use and operability of the monitoring device is improved.

When the parameters of interest for each anesthetic phase are displayed by means of trend graphs, according to this embodiment, for each anesthetic phase, basic physiological parameters such as heart rate (HR) and blood pressure (BP) are generally included.

In this embodiment, the phase indication icon of the anesthetic state display area is triggered to generate the request information for requesting display of the designated anesthetic phase. In a further embodiment, it is also possible to arrange a corresponding button or a knob or slide switch with different settings on the monitoring device to generate the corresponding request information. As an example, different buttons correspond to different anesthetic phases, and the corresponding request information is generated by selecting the button. As another example, for the knob or slide switch with different settings, the different settings represent different anesthetic phases. When the knob or slide switch is switched to a certain setting, the request information for the anesthetic phase corresponding to the setting is generated.

Second Embodiment

In the first embodiment, the request information for requesting display of the designated anesthetic phase needs to be manually triggered by the operator. By contrast, in the second embodiment, the request information for requesting display of the designated anesthetic phase is automatically generated by the monitoring device, e.g., generated in such a way that the signal collection module detects a distinctive operation or state for each phase. Each phase has an operation or state that is different from the other phases. When these operations or states occur, it means that the operations or states can be used as the distinctive operations or states of the phases at the end of the previous phase and the beginning of the subsequent phase.

As an example, the detection of a patient breathing support mode from a manual mode (gripping a ball by a hand) into a machine control mode means that the endotracheal intubation is completed and the surgery is about to begin, so the breathing of the patient into the machine control mode can be used as the distinctive operation or state for the anesthetic maintenance phase. As another example, the detection of the monitored value of neuromuscular transmission (NMT) of the patient being 0 for a certain period of time is used as a distinctive operation or state for the anesthetic maintenance phase. For example, the detection of the monitored value of concentration of an inhaled anesthetic drug being 0 or (and) an infusion pump being stopped to provide an anesthetic is used as a distinctive operation or status for the postoperative recovery phase. It is suitable for a single anesthesia mode or for a combined anesthesia mode. As another example, the detection of the monitored value of the bispectral index (BIS) of the patient being 80 or more is used as the distinctive operation or state for the postoperative recovery phase.

In this embodiment, the signal collection module further includes a first detection component for detecting the state of a respirator and a second detection component for detecting the state of the infusion pump. The first detection component and the second detection component are connected to the data processing module, and the data processing module generates, according to detection results of the first detection component and the second detection component, request information for requesting display of the anesthetic maintenance phase and request information for requesting display of the postoperative recovery phase.

As an example, when the first detection component detects that the breathing of the patient enters the machine control mode, the level state of the first detection component is reversed and a pulse is output to the data processing module, and the data processing module switches, based on the pulse, the display content of the anesthetic state display area from the anesthetic induction phase to the anesthetic maintenance phase, and displays the visualized information about the parameters of interest for the anesthetic maintenance phase. When the second detection component detects that the infusion pump stops administrating the anesthetic, the level state of the second detection component is reversed and a pulse is output to the data processing module. The data processing module switches, based on the pulse, the display content of the anesthetic state display area from the anesthetic induction phase or the anesthetic maintenance phase to the postoperative recovery phase, and displays the visualized information about the parameters of interest for the postoperative recovery phase.

Third Embodiment

Figure 8:
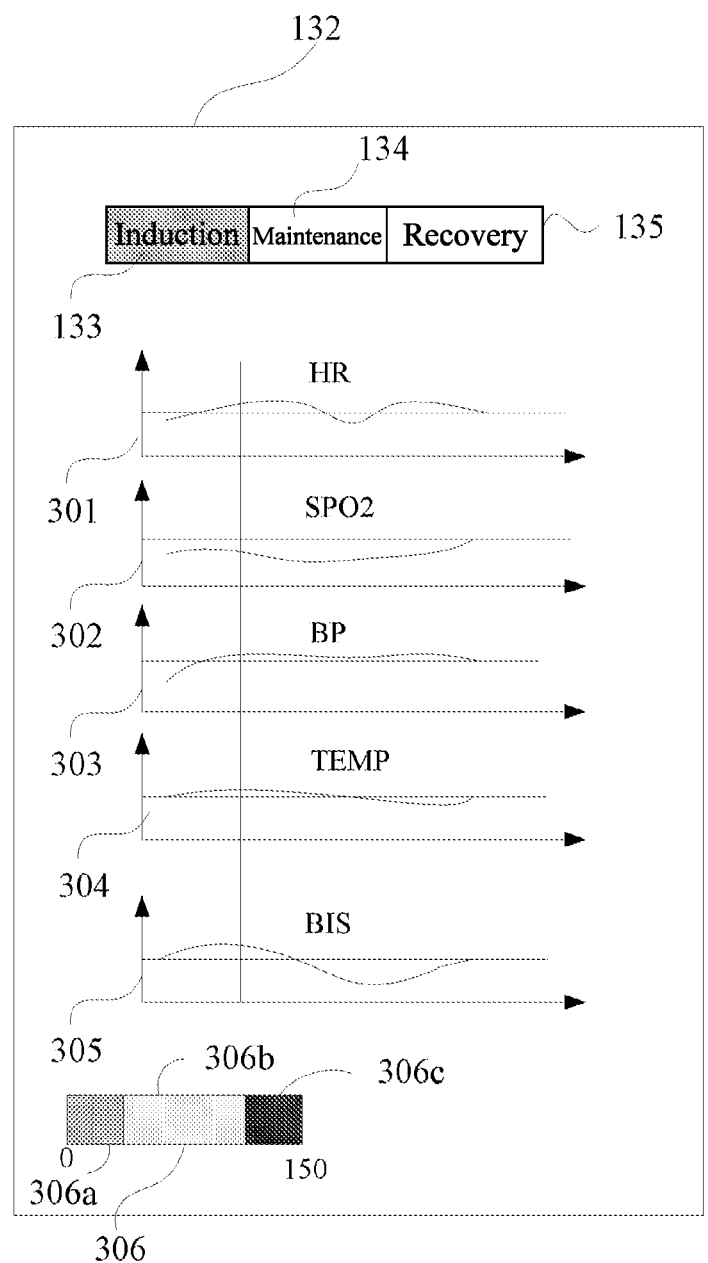
FIGS. 8, 9 and 10 are parameter trend graphs with baselines for the anesthetic induction phase, the anesthetic maintenance phase, and the postoperative recovery phase, respectively.
Figure 9:
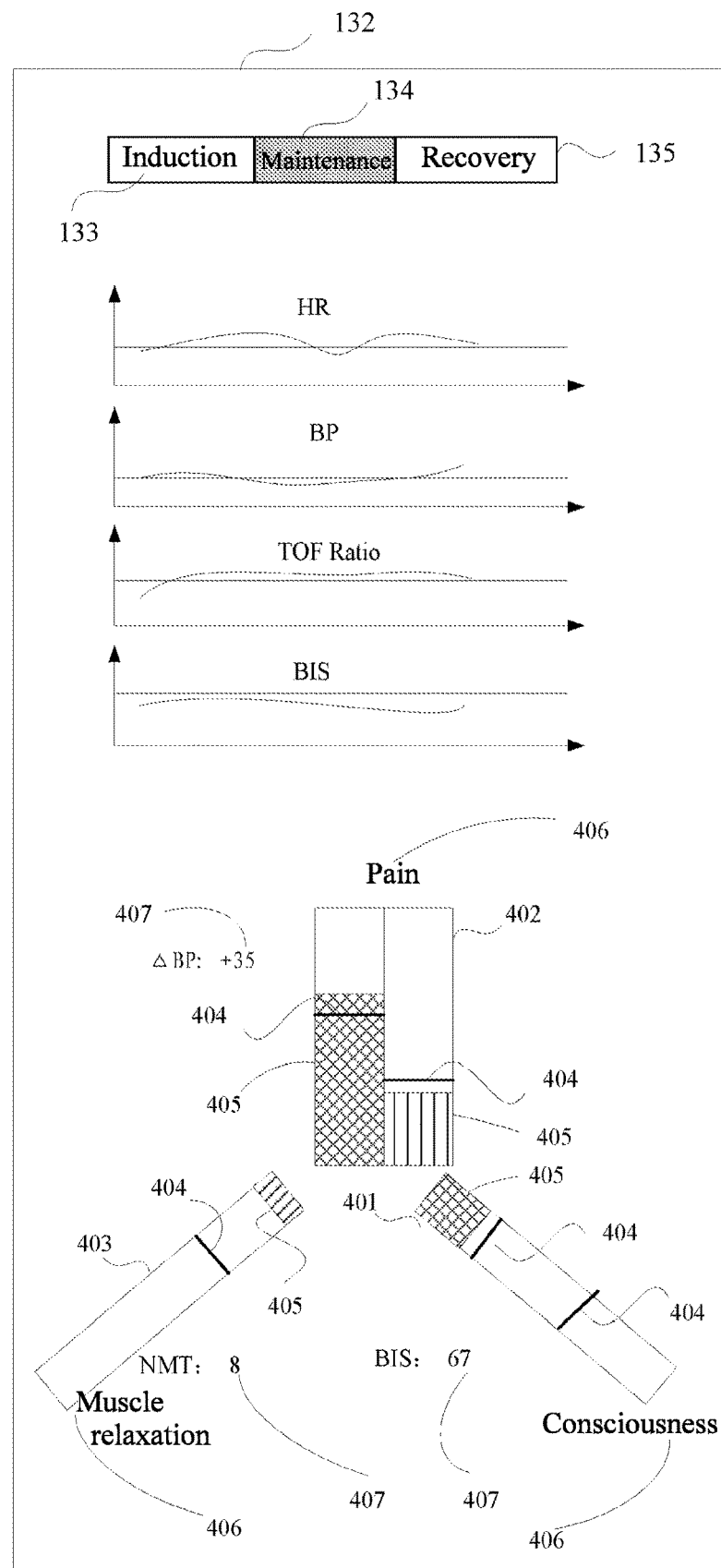
Figure 10:
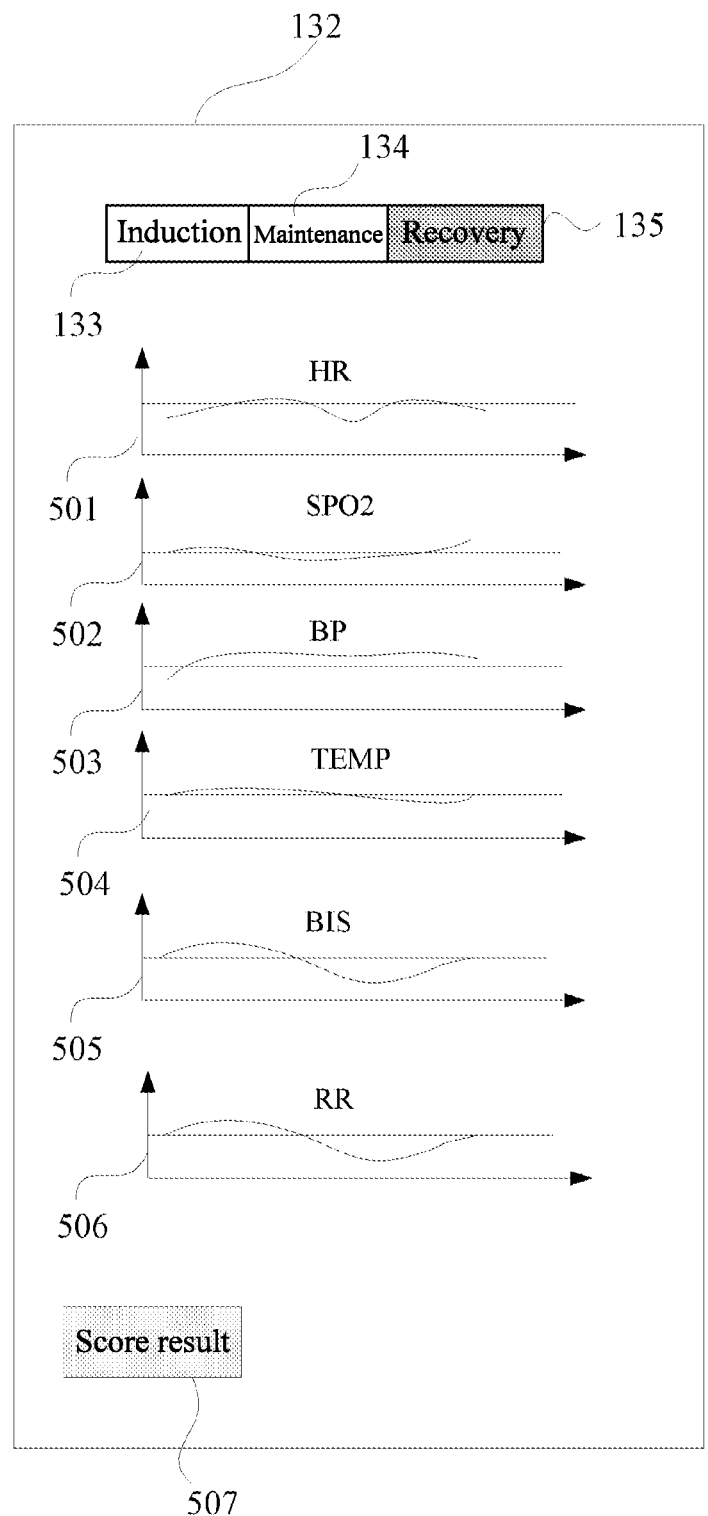

As shown in FIGS. 8, 9 and 10, this embodiment differs from the above embodiments in that a baseline parallel to a time axis is displayed on the trend graph. Trend graphs of the parameters for the anesthetic induction phase are shown in FIG. 8; trend graphs of the parameters for the anesthetic maintenance phase are shown in FIG. 9; and trend graphs of the parameters for the postoperative recovery phase are shown in FIG. 10. The value of the baseline may be the average value of a respective parameter of interest for a determined period of time before the beginning of the anesthetic induction phase, a value of the respective parameter of interest at a set time point or a pre-set value of the respective parameter of interest, the set time point may be, for example, the anesthetic induction phase start time.

In this embodiment, when it is detected that the start icon for initiating the anesthesia monitoring is triggered, the data processing module obtains the parameters of interest for all the anesthetic phases according to the currently detected physiological parameters and takes the parameters of interest at this moment as the reference values. Alternatively, when it is detected that the start icon for initiating the anesthesia monitoring is triggered, the data processing module obtains the parameters of interest for all the anesthetic phases according to the average values of the various physiological parameters previously measured within a period of time and then takes the parameters of interest at this moment as the reference values.

When the data processing module receives the request information for requesting display of the designated anesthetic phase, the parameters of interest corresponding to the designated anesthetic phase are obtained based on the request information. The reference value of each parameter of interest corresponding to the designated anesthetic phase is obtained based on the request information. The reference values and the parameters of interest are then processed into visualized information and output to the display module, and the display module displays the parameters of interest in the form of trend graphs, and displays, on the trend graphs, the reference values in the form of baselines parallel to the time axis.

In addition, when it is detected that the start icon for initiating the anesthesia monitoring is triggered, the data processing module further acquires the current time, and takes the current time as the start time of the anesthetic induction phase. When the data processing module receives the request information for requesting display of the anesthetic induction phase, an event line perpendicular to the time axis is also displayed on the trend graph, indicating that the anesthetic induction phase starts from this moment, as shown in FIG. 8.

Displaying the baseline on the trend graph can facilitate the physician in comparing the various parameters of the patient with the baselines corresponding to the parameters to understand the patient's changes in vital signs after anesthesia relative to those before anesthesia, which facilitates the physician in determining whether the condition of the patient is appropriate.

Fourth Embodiment

Figure 11:
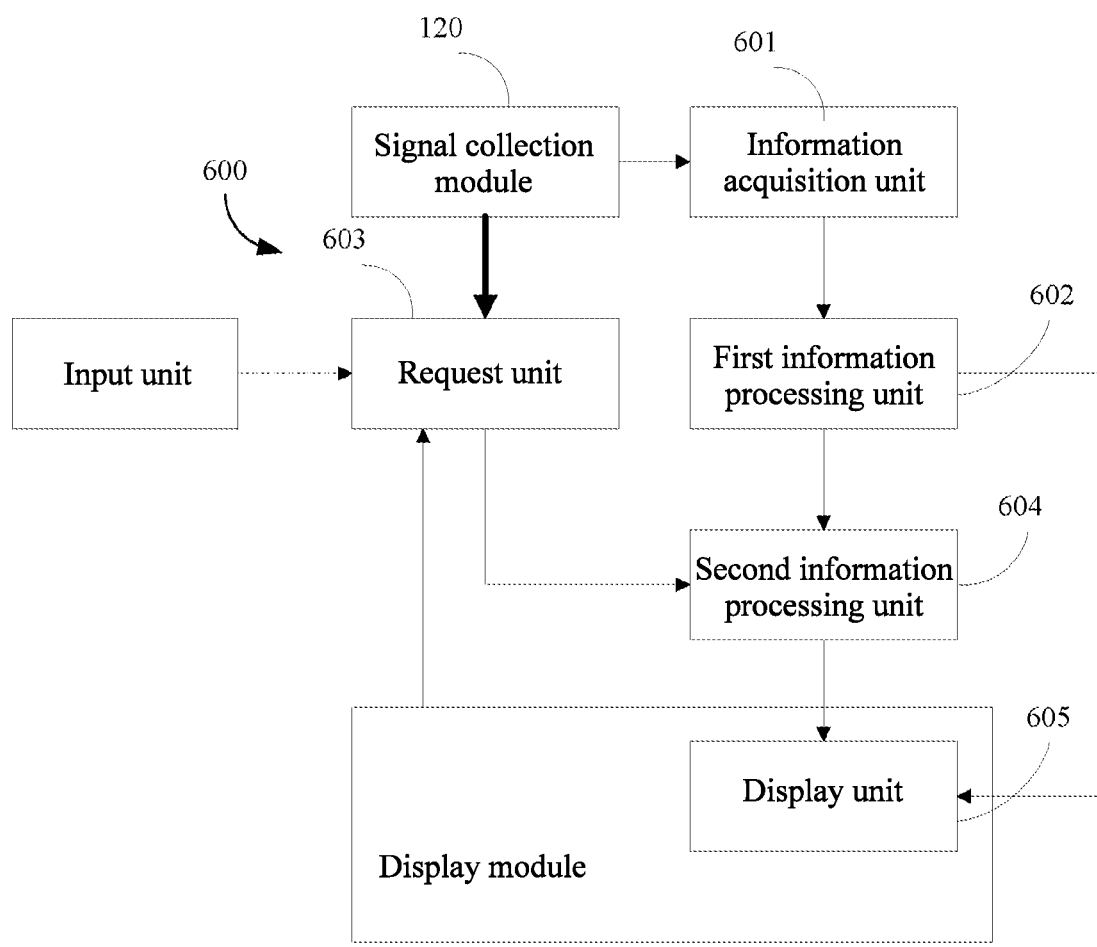
FIG. 11 is a schematic structural diagram of a patient monitoring information display system in one embodiment.

In this embodiment, a system for displaying patient anesthesia monitoring information is provided. Referring to FIG. 11, the system for displaying patient monitoring information 600 includes an information acquisition unit 601, a first information processing unit 602, a request unit 603, a second information processing unit 604, and a display unit 605.

In one embodiment, the information acquisition unit 601 may be connected to an output end of the signal collection module 120 and is configured to obtain vital sign signals collected by the signal collection module 120 from the body of the patient. The conventional vital sign signals include a pulse signal, a body temperature signal, a blood absorption signal for a specific band of light, an electrocardiogram signal, an electroencephalogram signal, etc.

The first information processing unit 602 is connected to the information acquisition unit 601, and is configured to process the vital sign signals to generate physiological parameters for reflecting the condition of the patient. The conventional physiological parameters include, for example, blood pressure, blood oxygen saturation, heart rate, body temperature, electrocardiogram, respiratory rate, etc.

The request unit 603 is configured to receive request information for requesting display of a designated anesthetic phase, the designated anesthetic phase being an anesthetic induction phase before surgery, an anesthetic maintenance phase during surgery, or a postoperative recovery phase after surgery. In one embodiment, the request information is generated based on a selection operation performed by the operator on the display interface, and thus the request unit 603 is connected to the display module 130, as shown by the solid line in FIG. 11.

In another embodiment, the request information is generated based on the operator switching the state of an input unit provided on the monitoring device, and thus the request unit 603 is connected to the input unit, and the input unit may be a button, a knob or slide switch having different settings, etc., as shown by the dotted line in FIG. 11.

In yet another embodiment, the request information is generated based on the signal collection module detecting a distinctive operation or state for each stage, and thus the request unit 603 is connected to the signal collection module 120, as shown by the bold line in FIG. 11.

The second information processing unit 604 is connected to the request unit 603 and the first information processing unit 602, and is configured to generate, based on the request information, visualized information about parameters of interest corresponding to the designated anesthetic phase, the parameters of interest including parameters selected from the physiological parameters and/or anesthetic parameters derived from the physiological parameters.

Each anesthetic phase has its own corresponding parameters of interest. The parameters of interest for the anesthetic induction phase include at least heart rate, blood oxygen saturation and blood pressure, and may further include at least one of body temperature, a bispectral index and a patient suffocation time. The parameters of interest for the anesthetic maintenance phase include at least a consciousness parameter characterizing the consciousness condition of the patient under anesthesia, a pain parameter characterizing the pain condition of the patient under anesthesia, and a muscle relaxation parameter characterizing the neuromuscular transmission condition of the patient under anesthesia. The consciousness parameter includes the bispectral index and/or a minimum alveolar concentration value; the pain parameter includes a blood pressure change and/or a heart rate change; and the muscle relaxation parameter includes neuromuscular transmission.

The parameters of interest for the anesthetic maintenance phase may further include the blood pressure and the heart rate. The parameters of interest for the postoperative recovery phase include at least heart rate, blood oxygen saturation and blood pressure. The parameters of interest for the postoperative recovery phase may further include a postoperative score result.

The display unit 605 is at least a part of the display module for displaying display data in a suitable manner on the display screen. The second information processing unit 604 is further connected to the display unit 605, and outputs the visualized information about the parameters of interest corresponding to the designated anesthetic phase to the display unit 605, such that the visualized information is displayed in an anesthetic state display area, the anesthetic state display area being at least a partial area of a display interface of a monitoring device.

As an example, in order to facilitate the physician in observing real-time data and historical data of the parameters such as the heart rate, the blood oxygen saturation, the blood pressure and the bispectral index of the patient, the second information processing unit 604 outputs data to the display unit 605 when the parameters of interest are displayed, so that the display unit 605 displays two-dimensional trend graphs of the parameters of interest in the anesthetic state display area.

To help the physician understand the patient's perception of pain during surgery (i.e., the anesthetic maintenance phase), the second information processing unit 604 outputs data to the display unit 605, such that current parameter values of the consciousness parameter, the pain parameter and the muscle relaxation parameter are respectively displayed in the form of a graph and/or a text in the anesthetic state display area by the display unit 605.

To help the physician intuitively understand the patient suffocation time during the endotracheal intubation, the second information processing unit 604 outputs data to the display unit 605, such that the patient suffocation time is displayed in the form of a time progress bar in the anesthetic state display area by the display unit 605.

To help the physician understand the postoperative recovery condition of the patient, the second information processing unit 604 outputs data to the display unit 605, such that the postoperative score result is displayed in the form of a selectable icon in the anesthetic state display area by the display unit 605.

When the display module detects that the icon is selected, the selected information is sent to the second information processing unit 604, and the second information processing unit 604 outputs the data to the display unit 605, such that the display unit 605 pops up a score sheet, the score sheet including a score for each item and a total score.

In another embodiment, the display interface is divided into at least two parts, one of which is an anesthetic state display area and the other is a conventional physiological parameter display area. The first information processing unit 602 is further connected to the display unit 605, and processes the conventional physiological parameters into visualized data and outputs same to the display unit, which displays the display data of the conventional physiological parameters in a suitable manner in the conventional physiological parameter display area.

The patient monitoring information display system can either be implemented by means of the programs described in the above embodiments, or by hardware, for example, by using gate circuits to build an application-specific integrated circuit. Those skilled in the art will appreciate that various programs in the foregoing embodiments may be stored in a computer readable storage medium, the storage medium may include: a read-only memory, a random access memory, a magnetic disk or an optical disk, etc., and the data processing module may implement the above functions by executing the programs using a microprocessor.

The present disclosure has been described in detail with reference to specific examples, which are merely for the purpose of facilitating understanding of the present disclosure and are not intended to limit the present disclosure. It will be apparent to those skilled in the art that changes may be made to the specific embodiments described above in accordance with the teachings of the present disclosure.

What is claimed is:

1. A medical monitoring device, comprising:
   physiological sensors configured to collect vital sign signals from a body of a patient;
   a processor connected to the physiological sensors and configured to receive the vital sign signals and process the vital sign signals to generate physiological parameters for reflecting a condition of the patient, the processor being further configured to receive request information for requesting display of a designated anesthetic phase and generate, based on the request information, parameters of interest corresponding to the designated anesthetic phase, the designated anesthetic phase being an anesthetic induction phase before surgery, an anesthetic maintenance phase during surgery, or a postoperative recovery phase after surgery, and the parameters of interest comprising parameters selected from the physiological parameters and/or anesthetic parameters derived from the physiological parameters; and
   a display screen configured to display a display interface, the display interface comprising an anesthetic state display area and a conventional display area, the anesthetic state display area and the conventional display area being simultaneously displayed together on the display screen with phase indication icons, one of the phase indication icons indicating the designated anesthetic phase; the display screen being connected to the processor and configured to display the physiological parameters in the conventional display area and further display in the anesthetic state display area the parameters of interest corresponding to the designated anesthetic phase; wherein the phase indication icons are selectable to change the designated anesthetic phase and generate the request information.

2. The medical monitoring device of claim 1, wherein at least one of the parameters of interest corresponding to the designated anesthetic phase is displayed at least in a form of a trend graph in the anesthetic state display area, the trend graph representing a trend of values of at least one of the parameters of interest over time in the designated anesthetic phase.

3. The medical monitoring device of claim 2, wherein a baseline parallel to a time axis is displayed on the trend graph, a value of the baseline is capable of being an average value of a respective parameter of interest for a determined period of time before a beginning of the anesthetic induction phase, a value of the respective parameter of interest at a set time point or a pre-set value of the respective parameter of interest; and
wherein an event line representing an anesthetic induction phase start time is further displayed on the trend graph, the event line being perpendicular to the time axis.

4. The medical monitoring device of claim 2, wherein the designated anesthetic phase is the anesthetic induction phase, and the parameters of interest for the anesthetic induction phase include at least a heart rate, a blood oxygen saturation and a blood pressure; and
wherein the designated anesthetic phase is the anesthetic maintenance phase, and the parameters of interest for the anesthetic maintenance phase include at least a consciousness parameter characterizing consciousness condition of the patient under anesthesia, a pain parameter characterizing pain condition of the patient under anesthesia, and a muscle relaxation parameter characterizing neuromuscular transmission condition of the patient under anesthesia, current parameter values of the consciousness parameter, the pain parameter, and the muscle relaxation parameter being respectively displayed as a graph and/or a text in the anesthetic state display area; and
wherein the designated anesthetic phase is the postoperative recovery phase, and the parameters of interest for the postoperative recovery phase include at least a heart rate, a blood oxygen saturation and a blood pressure, a heart rate, a blood oxygen saturation and a blood pressure being respectively displayed as trend graphs in the anesthetic state display area.

5. The medical monitoring device of claim 4, wherein the parameters of interest for the anesthetic induction phase further include a body temperature and a bispectral index, and the heart rate, the blood oxygen saturation, the blood pressure, the body temperature and the bispectral index are respectively displayed as trend graphs in the anesthetic state display area.

6. The medical monitoring device of claim 4, wherein the parameters of interest for the anesthetic induction phase further include a patient suffocation time, the patient suffocation time is displayed as a time progress bar in the anesthetic state display area, at least a warning zone and a danger zone are marked on a time bar in a time progress direction, the warning zone represents a period of time for which the patient is allowed to suffocate, a length of time of the warning zone is set according to a type of the patient, and the danger zone represents a period of suffocation time for which the patient may be in danger; when the physiological sensors detects a respiratory signal, the processor starts timing and outputs a display signal such a progress pointer is moved along the time bar according to the timing time from the 0 coordinate of the time bar; and when a next respiratory signal is detected, the processor outputs a display signal that resets the progress pointer to the 0 coordinate.

7. The medical monitoring device of claim 4, wherein the consciousness parameter comprises a bispectral index and/or a minimum alveolar concentration, the pain parameter comprises a blood pressure change and/or a heart rate change, and the muscle relaxation parameter comprises neuromuscular transmission, the blood pressure change being a change in a blood pressure relative to a blood pressure reference value, and the heart rate change being a change in a heart rate relative to a heart rate reference value; and
wherein the parameters of interest for the anesthetic maintenance phase further comprise the blood pressure and the heart rate, and the bispectral index, the minimum alveolar concentration, the neuromuscular transmission, the blood pressure and the heart rate which are respectively displayed as trend graphs in the anesthetic state display area.

8. The medical monitoring device of claim 4, wherein the parameters of interest for the postoperative recovery phase also comprise a postoperative score result, which is displayed as an icon in the anesthetic state display area, and a score sheet is popped up on the display interface when the processor detects that the icon is selected, the score sheet comprising a score for each item and a total score.

9. The medical monitoring device of claim 1, wherein the phase indication icons in the anesthetic state display area respectively represent at least two of the anesthetic induction phase, the anesthetic maintenance phase and the postoperative recovery phase, and
wherein request information for the anesthetic maintenance phase is generated when it is detected that breathing of the patient enters a machine control mode, and request information for the postoperative recovery phase is generated when an operation is detected.

10. A method for displaying patient monitoring information, comprising:
acquiring vital sign signals collected from a body of a patient;
processing the vital sign signals to generate physiological parameters for reflecting condition of the patient;
displaying the physiological parameters in a conventional display area of a display screen of a monitoring device;
displaying phase indication icons in an anesthetic state display area of the display screen, one of the phase indication icons indicating a designated anesthetic phase selected from the group consisting of an anesthetic induction phase before surgery, an anesthetic maintenance phase during surgery, or a postoperative recovery phase after surgery,
generating request information for requesting display of a designated anesthetic phase when one of the phase indication icons is selected;
providing, based on the request information, parameters of interest corresponding to the designated anesthetic phase, the parameters of interest comprising parameters selected from the physiological parameters and/or anesthetic parameters derived from the physiological parameters; and
displaying in the anesthetic state display area the parameters of interest corresponding to the designated anesthetic phase, the parameters of interesting being displayed simultaneously on the display screen with the phase indication icons in the anesthetic state display area and the physiological parameters in the conventional display area.

11. The method of claim 10, wherein at least one of the parameters of interest corresponding to the designated anesthetic phase is displayed at least in a form of a trend graph in the anesthetic state display area, the trend graph representing a trend of values of at least one of the parameters of interest over time in the designated anesthetic phase.

12. The method of claim 11, further comprising:
acquiring a reference value of each parameter of interest for the designated anesthetic phase, a value of a baseline is an average value of a respective parameter of interest for a determined period of time before a beginning of the anesthetic induction phase, a value of the respective parameter of interest at a set time point or a pre-set value of the respective parameter of interest; and
displaying, on the trend graph, the reference value as the baseline parallel to a time axis; and
wherein acquiring a start time of the anesthetic induction phase, and displaying, on the trend graph, the start time as an event line perpendicular to the time axis.

13. The method of claim 11, wherein the designated anesthetic phase is the anesthetic induction phase, and the parameters of interest for the anesthetic induction phase comprise at least a heart rate, a blood oxygen saturation and a blood pressure; and
wherein the designated anesthetic phase is the anesthetic maintenance phase, and the parameters of interest for the anesthetic maintenance phase comprise at least a consciousness parameter characterizing consciousness condition of the patient under anesthesia, a pain parameter characterizing pain condition of the patient under anesthesia, and a muscle relaxation parameter characterizing neuromuscular transmission condition of the patient under anesthesia, current parameter values of the consciousness parameter, the pain parameter, and the muscle relaxation parameter being respectively displayed as a graph and/or a text in the anesthetic state display area; and
wherein the designated anesthetic phase is the postoperative recovery phase, and the parameters of interest for the postoperative recovery phase comprise at least a heart rate, a blood oxygen saturation and a blood pressure, a heart rate, a blood oxygen saturation and a blood pressure being respectively displayed as trend graphs in the anesthetic state display area.

14. The method of claim 13, wherein the parameters of interest for the anesthetic induction phase further comprise a body temperature and a bispectral index, and the heart rate, the blood oxygen saturation, the blood pressure, the body temperature and the bispectral index are respectively displayed as trend graphs in the anesthetic state display area; or
wherein the parameters of interest for the anesthetic induction phase further comprise a patient suffocation time, the patient suffocation time being displayed as a time progress bar or values in the anesthetic state display area.

15. The method of claim 14, wherein the patient suffocation time being displayed as the time progress bar in the anesthetic state display area comprises:
marking at least a warning zone and a danger zone on the time bar in a time progress direction, the warning zone representing a period of time for which the patient is allowed to suffocate, a length of time of the warning zone being set according to a type of the patient, and the danger zone representing a period of suffocation time for which the patient may be in danger; and
acquiring a respiratory signal of the patient, starting timing when the respiratory signal is detected, moving a progress pointer along the time bar according to the timing time from the 0 coordinate of the time bar, and resetting the progress pointer to the 0 coordinate when a next respiratory signal is detected.

16. The method of claim 15, wherein a breathing alarm is masked or a breathing alarm threshold is altered such that the breathing alarm threshold is greater than or equal to a maximum time value of the warning zone, when the patient suffocation time is detected.

17. The method of claim 13, wherein the consciousness parameter comprises a bispectral index and/or a minimum alveolar concentration, the pain parameter comprises a blood pressure change and/or a heart rate change, and the muscle relaxation parameter comprises neuromuscular transmission, the blood pressure change being a change in a blood pressure relative to a blood pressure reference value, and the heart rate change being a change in a heart rate relative to a heart rate reference value; and
wherein the parameters of interest for the anesthetic maintenance phase further comprise the blood pressure and the heart rate, and the bispectral index, the minimum alveolar concentration, the neuromuscular transmission, the blood pressure and the heart rate which are respectively displayed as trend graphs in the anesthetic state display area.

18. The method of claim 13, wherein the parameters of interest for the postoperative recovery phase also comprise a postoperative score result, which is displayed as an icon in the anesthetic state display area, and a score sheet is popped up when it is detected that the icon is selected, the score sheet comprising a score for each item and a total score.

19. The method of claim 10, wherein the request information for requesting display of the designated anesthetic phase is generated by means of manual triggering; or
wherein the request information for requesting display of the designated anesthetic phase is generated in such a way that a distinctive operation or state for each phase is detected.

20. The method of claim 19,
wherein the phase indication icons represent at least two of the anesthetic induction phase, the anesthetic maintenance phase and the postoperative recovery phase; and
wherein request information for requesting display of the anesthetic maintenance phase is generated when it is detected that breathing of the patient enters a machine control mode, and request information for requesting display of the postoperative recovery phase is generated when an operation is detected.

* * * * *